United States Patent
Van Veen et al.

(10) Patent No.: US 9,162,211 B2
(45) Date of Patent: Oct. 20, 2015

(54) MICRO-REACTOR FOR OBSERVING PARTICLES IN A FLUID

(75) Inventors: Gerard Anne Nicolaas Van Veen, Waalre (NL); Jacobus Peter Johannes Peters, Amsterdam (NL); Pleun Dona, Veldhoven (NL); Alan Frank De Jong, Eindhoven (NL)

(73) Assignee: FEI Company, Hillsboro, OR (US)

( * ) Notice: Subject to any disclaimer, the term of this patent is extended or adjusted under 35 U.S.C. 154(b) by 408 days.

(21) Appl. No.: 12/912,468

(22) Filed: Oct. 26, 2010

(65) Prior Publication Data

US 2011/0097706 A1 Apr. 28, 2011

(30) Foreign Application Priority Data

Oct. 26, 2009 (EP) .................................. 09174002

(51) Int. Cl.
*G01N 15/14* (2006.01)
*G01N 21/05* (2006.01)
(Continued)

(52) U.S. Cl.
CPC ....... *B01J 19/0093* (2013.01); *B01L 3/502761* (2013.01); *H01J 37/20* (2013.01); *H01J 37/26* (2013.01); *B01J 2219/0086* (2013.01); *B01J 2219/0097* (2013.01); *B01J 2219/00783* (2013.01); *B01J 2219/00824* (2013.01);
(Continued)

(58) Field of Classification Search
CPC ......... G01N 15/14; G01N 15/1434–2015/144; G01N 2021/058
USPC .............................. 356/246, 409–411; 378/51
See application file for complete search history.

(56) References Cited

U.S. PATENT DOCUMENTS

| 5,415,841 A | 5/1995 | Dovichi et al. |
| 5,565,171 A | 10/1996 | Dovichi et al. |

(Continued)

FOREIGN PATENT DOCUMENTS

| JP | 2007-108075 | 4/2007 |
| WO | 2005089253 | 9/2005 |

(Continued)

OTHER PUBLICATIONS

Adam, Jean-Francois, et al., 'Table-Top Water Window Transmission X-Ray Microscopy: Review of the Key Issues, and Conceptual Design of an Instrument for Biology,' Review of Scientific Instruments, 2005, 15 pgs, vol. 76.

*Primary Examiner* — Michael A Lyons
*Assistant Examiner* — Rebecca C Bryant
(74) *Attorney, Agent, or Firm* — Scheinberg & Associates, PC; Michael O. Scheinberg; Nathan H. Calvert

(57) ABSTRACT

A micro-reactor is provided for observing small particles, cells, bacteria, viruses or protein molecules in a fluid. The micro-reactor includes a first channel for containing the fluid and a second channel adjacent to the first channel. A gap connects the first channel and the second channel and a window transparent to the method of inspection is provided at the gap. A static or dynamic gradient, such as a gradient in concentration of a chemical or biological material, in pressure, in temperature, in electric potential, or in magnetic field, is applied across the gap, thereby causing the particles to cross the gap. By detecting a property of the particles upstream in the first channel and then applying a pressure burst over the channels when the property meets certain pre-set criteria, only selected particles can be placed in the gap.

24 Claims, 3 Drawing Sheets

(51) Int. Cl.
  *B01J 19/00* (2006.01)
  *B01L 3/00* (2006.01)
  *H01J 37/20* (2006.01)
  *H01J 37/26* (2006.01)
  *B01L 7/00* (2006.01)

(52) U.S. Cl.
  CPC ............... *B01J2219/00831* (2013.01); *B01J 2219/00833* (2013.01); *B01J 2219/00905* (2013.01); *B01L 7/54* (2013.01); *B01L 2200/0668* (2013.01); *B01L 2300/0822* (2013.01); *B01L 2400/0415* (2013.01); *B01L 2400/0439* (2013.01); *B01L 2400/0442* (2013.01); *B01L 2400/0487* (2013.01); *G01N 2021/058* (2013.01); *H01J 2237/2004* (2013.01); *Y10T 436/143333* (2013.01)

(56) References Cited

U.S. PATENT DOCUMENTS

| | | | |
|---|---|---|---|
| 5,986,270 | A | 11/1999 | Bormans et al. |
| 6,193,647 | B1 | 2/2001 | Beebe et al. |
| 6,432,290 | B1 | 8/2002 | Harrison et al. |
| 6,695,765 | B1 | 2/2004 | Beebe et al. |
| 7,259,846 | B2 * | 8/2007 | Schembri et al. ............ 356/246 |
| 2004/0256318 | A1 | 12/2004 | Iida et al. |
| 2008/0179518 | A1 | 7/2008 | Creemer et al. |
| 2009/0129198 | A1 * | 5/2009 | Karaki et al. ................ 366/145 |
| 2011/0006208 | A1 | 1/2011 | Freitag et al. |

FOREIGN PATENT DOCUMENTS

| | | |
|---|---|---|
| WO | 2006/031104 | 3/2006 |
| WO | 2006052882 | 5/2006 |
| WO | 2011009209 | 1/2011 |

* cited by examiner

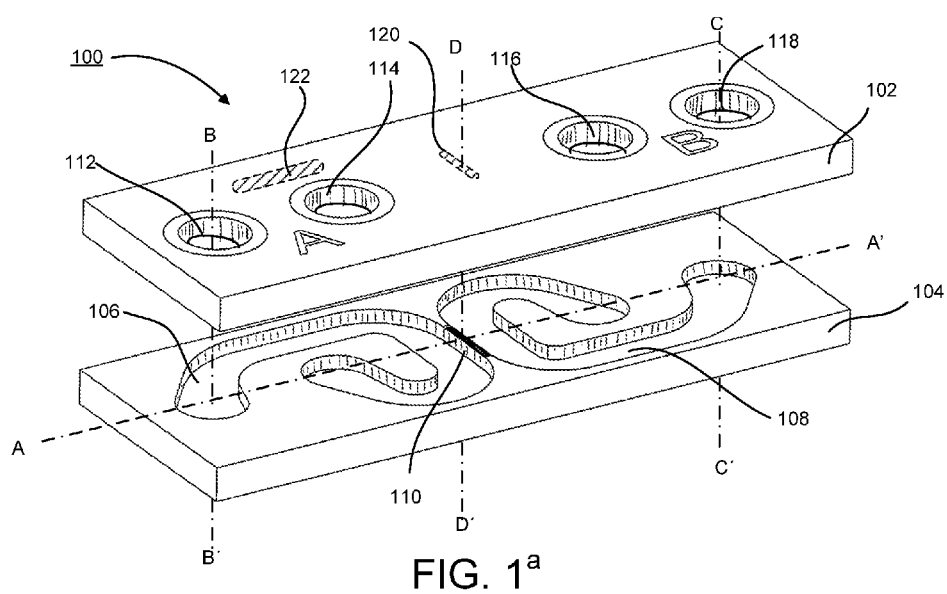
FIG. 1$^a$
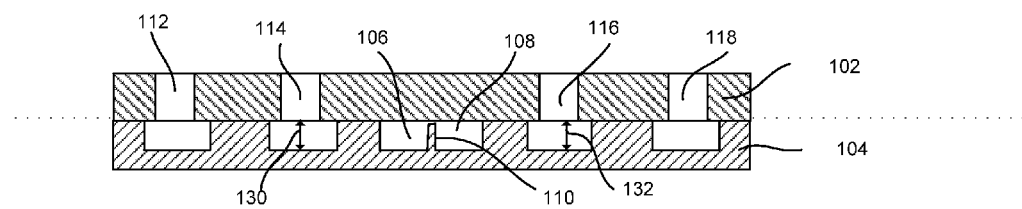
FIG. 1$^b$

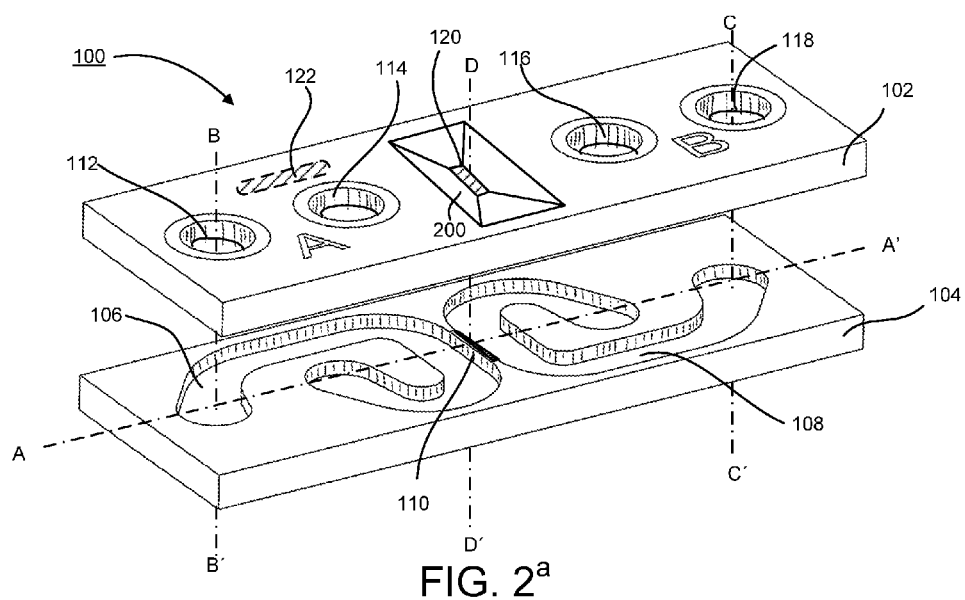
FIG. 2ᵃ
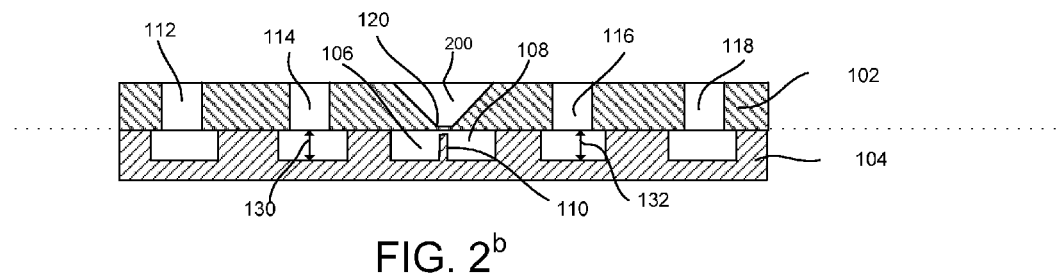
FIG. 2ᵇ

MICRO-REACTOR FOR OBSERVING PARTICLES IN A FLUID

The invention relates to a micro-reactor for observing particles or parts thereof in a fluid, parts of the micro-reactor showing transparency for a method of inspection, the micro-reactor comprising a first channel formed between two layers for containing the fluid, the first channel comprising an inlet and an outlet, at the first channel the two layers being separated by a first distance.

The invention further relates to a method of using said micro-reactor.

Such a micro-reactor is known from European application No. EP05787328.

The known patent application discloses a micro-reactor for use in a Transmission Electron Microscope (TEM). The micro-reactor comprises two so-named cover layers that are kept a small distance apart from each other with spacers. The two cover layers thus define a channel, to which channel an inlet and an outlet is provided. Hereby a fluid can be introduced in the channel. Each cover layer shows a multitude of recesses that are sufficiently thin to be transparent for the electrons used in the TEM. The recesses are placed in such a manner, that an electron beam impinging perpendicular to a cover layer and travelling through one recess also passes through a corresponding recess in the other cover layer. Thereby the fluid and any particles and/or cells within the fluid between two corresponding recesses can be observed by the TEM.

It is noted that, in the context of this invention, the phrase "particles" includes catalyst particles, geological particles, organic particles including biological cells, bacteria, and viruses, as well as protein molecules, DNA, etc, and parts of said particles, such as organelles.

A disadvantage of the known micro-reactor is that the total surface area of all recesses transparent to electrons is only a fraction of the surface area of the cover layer. As a result the major part of the channel is invisible to the TEM. It is even possible for particles or cells to travel from inlet to outlet without passing between recesses, and thus without a chance for the TEM to observe them. Another, related, problem is that there are no means to position the particles or cells within the micro-reactor.

This makes working with the known micro-reactor a time consuming job, without any guarantee that a specific particle or cell is identified or even becomes visible.

The invention intends to provide a micro-reactor in which the particles or samples can be positioned.

To that end a micro-reactor according to the invention is characterized in that the micro-reactor further comprises
  a second channel adjacent to the first channel, the second channel comprising an outlet, the two layers at the second channel being separated by a second distance,
  a gap connecting the first channel and the second channel,
  at the gap at least one layer showing a window transparent to the method of inspection, and
  at the window the two layers being separated by a third distance smaller than the first distance and smaller than the second distance,
  at the gap at least one of the layers showing transparency for the method of observation, and
  the third distance being equal to or smaller than the operating range of the method of inspection.

By having a second channel with an outlet, and a gap connecting the two channels, particles and/or cells in the fluid can be positioned in the gap, e.g. by controlled pressure differences between the channels. As a result a particle or cell can be positioned in the gap, more specifically to the window (that may cover the whole gap, or a part of the gap only) to be inspected there.

The third distance, separating the two layers at the gap, is limited to the operating range of the method of inspection.

When using an optical microscope the third distance may be equal to or less than the depth of focus. When using an electron microscope the third distance may be equal to or less than the penetration range of the electrons.

It is noted that the window material, the type of fluid, particles and cells all influence the maximum usable third distance.

Also inspection with, for example, neutrons, or electromagnetic radiation outside the band of visible light, including e.g. X-rays, is envisaged.

In an embodiment of the micro-reactor according to the invention the method of inspection comprises inspection with a microscope and the operating range of the method of inspection is the depth of focus of the microscope.

Here the micro-reactor is used in conjunction with an optical microscope and the height of the gap, the third distance, is equal to or less than the focal depth of the microscope. As a result all particles or cells in gap and in the field of view of the microscope are in focus.

It is noted that in this context optical microscopy includes, but is not limited to, phase contrast microscopy, laser confocal microscopy, and fluorescent microscopy, and the optical microscope includes the optical microscope used for these types of microscopy.

In another embodiment of the micro-reactor according to the invention the method of inspection comprises inspection by irradiating the micro-reactor with a beam of particles or X-rays, and the operating range of the method of inspection is the penetration depth of the particles or X-rays irradiating the micro-reactor.

When inspecting with an electron microscope, for example a Transmission Electron Microscope (TEM), a Scanning Transmission Electron Microscope (STEM), or a Scanning Electron Microscope (SEM), the micro-reactor is irradiated by electrons. The energy of the electrons may vary. A SEM is typically equipped to operate with electrons with an energy below 50 keV, while a STEM and a TEM are typically equipped to operate with electrons with an energy above 30 keV, typically up to 300 or 400 keV.

It is noted that also other particles, such as high energy protons, can be used to irradiate the micro-reactor.

The particles irradiating the micro-reactor, and penetrating in the gap, will cause secondary radiation to emerge from the fluid, particles and cells present in the gap. This secondary radiation comprises back-scattered electrons, X-rays, scattered electrons and photons (due to, e.g., fluorescence). Part of this secondary radiation may leave the gap, to be detected by detectors. Also some electrons may travel through the gap, either diffracted or virtually unhindered, to be detected by a detector.

In this way information of the composition of fluid, particles and cells in the gap can be obtained.

It is noted that, for secondary radiation to occur, the electrons should at least enter the gap, that is: should at least travel though the material of the window. The electrons then enter the fluid, particles and/or cells, and cause secondary radiation there. This radiation should then leave the gap through one of the layers, to be detected.

Similarly, when irradiating the micro-reactor with soft X-rays, such as the X-rays with an energy below, for example, 600 eV, the penetration of these X-rays is limited to several micrometers. As an example: 30% of 500 eV photons is transmitted through 10 µm of water. The use of such low energy X-ray quanta, with an energy between the carbon K-edge of 284 eV and the oxygen K-edge of 543 eV, results in images with relatively high contrast between carbon rich structures and water is described in, for example, "Table-top water window transmission x-ray microscope: review of the key issues, and conceptual design of an instrument for biology", J. F. Adam et al., Review of Scientific Instruments 76, 091301 (2005), In another embodiment of the micro-reactor according to the invention the method of inspection comprises the detection of particles from the group of neutrons, secondary electrons, back-scattered electrons, and transmitted electrons; and/or photons from the group of infrared, visible light, UV or X-ray photons.

It is noted that the photons may be the direct result of impinging photons (including fluorescence), but may also result from e.g. impinging electrons. The use of electrons to excite fluorescence is well known from imaging so-named markers in biological applications.

In another embodiment of the micro-reactor according to the invention at least one layer bordering the gap is transparent to light.

When at least one layer is transparent to light the gap can be observed with reflected light. The other layer may also be transparent to light, or may, for example, be reflective.

In another embodiment of the micro-reactor according to the invention at least one layer bordering the gap is transparent to electrons.

When at least one layer is transparent to electrons, back-scattered electrons, X-rays, luminescence, etc. resulting from electrons impinging on the fluid through the transparent layer can be detected outside the gap.

In another embodiment of the micro-reactor according to the invention at least a part of the micro-reactor is formed from glass.

When using the micro-reactor in conjunction with an optical microscope, the micro-reactor is preferably made of glass. Glass has good optical properties, while its machinability by, for example, lithographic techniques, by sandblasting, or etching is well known However, the invention is not limited to micro-reactors of this material, as also certain polymers, and, for example, silicon nitride ($Si_3N_4$), silicon carbide (SiC), etc. may be used to build a micro-reactor.

In another embodiment of the micro-reactor according to the invention the third distance is less than 5 µm, more specifically less than 1 µm, most specifically less than 300 nm.

The height of the gap (the third distance) of 5 µm is typically for the focal depth of an optical microscope, while 1 µm is the lower limit for the depth of focus of light and UV fluorescence optical microscopy and the upper limit through which electrons can penetrate. A value of 300 to 500 nm must be seen as an upper value at which TEM and STEM microscopy can give high resolution images.

In another embodiment of the micro-reactor according to the invention the second channel comprises an inlet.

By having a second channel with an inlet and an outlet, the second channel can be flushed. Also this gives the opportunity to add to or flow through the first channel a first type of chemicals or cells, and another type of chemicals or cells to or through the second channel, and observing reactions between the chemicals or cells in the gap, that now acts as boundary between the two channels.

In still another embodiment the micro-reactor is equipped to be split in such a manner that one of the layers is removed from the gap.

By removing one of the layers from the gap, the matrix in which the particles and/or cells are suspended (which may be a frozen fluid at that moment), and the particles and/or cells within become available for other inspection methods (such as standard SEM inspection) or parts can be excised (mechanically or, for example, with a Focused Ion Beam) and, after thinning, be inspected in, for example, a TEM.

In an aspect of the invention a method of operating the micro-reactor according to the invention is characterized in that a gradient is applied to the gap, the gradient being a static or a dynamic gradient.

Applying a gradient, such as a pressure difference resulting in a movement of the fluid, is used to coax the particles or cells in the gap.

When applying a static gradient, e.g. a static pressure difference a part of the flow through the first channel can be tapped. Also, when the static difference is for example the result of the concentration of certain biological or chemical materials, cells can be coaxed to enter the gap, for example by adding a so-named attractor fluid, such as cytokine or chemokine, to one of the channels.

It is noted that is possible to coax a type of cells to travel from the first to the second channel, for example as a result of a first attractor fluid, while simultaneously another type of cells travel from the second to the first channel.

In an embodiment of the method according to the invention the gradient is a gradient in the concentration of a chemical, a gradient in the concentration of a biological material, a gradient in pressure, a gradient in temperature, a gradient in electrical potential or a magnetic field.

In another embodiment of the method according to the invention the gradient is a gradient in pressure and the gradient in pressure is generated by heating of the fluid so that a bubble forms or by moving a piezo-electric element.

This method of moving a fluid is well-known from, e.g., ink-jet printers. The heating may be caused by resistive heating, but also laser heating may be used.

In yet another embodiment of the method according to the gradient is a dynamic gradient, the gradient set to one of two preset values according to the result of a measurement or observation of a property, one of the preset values of the gradient resulting in particles and/or cells brought into the gap and the other preset value of the gradient resulting in the particles and/or cells not brought into the gap, resulting in only particles and/or cells with a predetermined property being brought into the gap.

By measuring or observing a property of the cells or particles moving through, for example, the first channel before they pass the gap, and use the observation to select particles and/or cells, only selected cells can be brought into the gap for further inspection.

In still a further embodiment of the method according to the invention the measurement or observation of a property is the measurement or observation of a property of the group of geometric properties, mechanical properties, concentration per volume, luminescence, fluorescence, phosphorescence, radioactivity, or colour, biological behaviour or chemical behaviour.

The observed property may be based on the form of the cell or particle, but also on its ability to show luminescence (for example as a result of a DC voltage difference over the layers of the first channel or RF coupling into the fluid), or any other of the mentioned properties. Also mechanical properties, such as elasticity, may be used by applying so-named 'laser pincers' to the particles.

In another embodiment of the method according to the invention the particles or cells brought into the gap are immobilized.

By immobilizing the particles and/or cells further inspection may be improved.

In a further embodiment of the method according to the invention the particles or cells are in a solution and the particles or cells are immobilized by freezing or polymerizing the solution. Freezing is a well-known method to immobilize cells or particles. It is mentioned that, when cooling water very rapidly from 0° C. to −170° C., ice without crystals (amorphous ice) is formed, and thus no damage by e.g. puncture of cell membranes occurs.

In an embodiment of the method according to the invention, after immobilizing the particles or cells, the micro-reactor is split in such a way that one of the layers is removed from the gap, and the particles and/or cells are inspected afterwards.

By removing one of the layers, the material in the gap becomes accessible to, for example, inspection with a Scanning Electron Microscope (SEM), a Focused Ion Beam machine (FIB), or other inspection methods that are hindered by the layer.

It is noted that the hindrance may be due to hindrance of, for example, the impinging particles, but may also be the result of hindrance of information carriers emitted from the material in the gap in response to the irradiation.

In a further embodiment a part of the frozen or polymerized fluid and/or cells and/or particles is excised from the gap, to be machined and/or inspected in another environment. Here a specific part of the material, e.g. a part of a cell that is already inspected in the gap, is excised. In further steps in may, for example, be thinned so as to be inspected in a TEM using high resolution TEM (for which samples with a thickness of less than 100 nm may be necessary).

BRIEF DESCRIPTION OF THE DRAWINGS

The invention is now described with reference to figures in which identical reference numerals denote corresponding elements. Here:

FIG. 1a schematically shows an exploded view of a micro-reactor according to the invention, FIG. 1b schematically shows a cross-section of the micro-reactor of FIG. 1a, FIG. 2a schematically shows an exploded view of a micro-reactor for use in a STEM, FIG. 2b schematically shows a cross-section of the micro-reactor of FIG. 2a, and FIG. 3 schematically shows a cross-section of the micro-reactor for use in a TEM.

FIG. 1a schematically shows an exploded view of a micro-reactor according to the invention.

FIG. 1a shows a micro-reactor 100, comprising a first layer 102 and a second layer 104. In the second layer a first channel 106 and a second channel 108 are formed, the two channels separated by a wall 110. When the first and the second layer are bonded, a small gap is left open between the first and the second channel above the wall.

Figure 3:
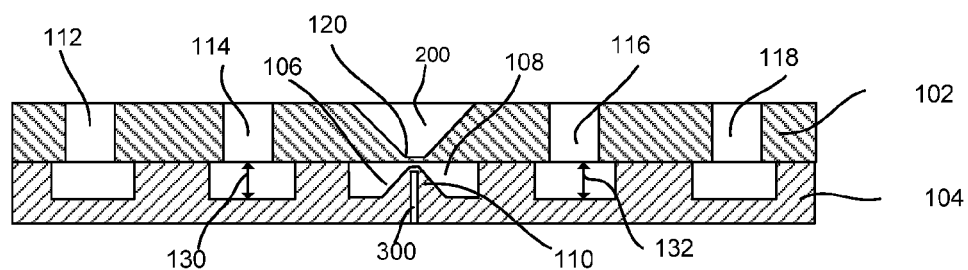

The first layer further shows an inlet 112 and an outlet 114, the inlet and the outlet formed by through-holes connecting to the first channel. Similarly an inlet 116 and an outlet 118 connect to the second channel.

FIG. 1b shows a cross-section of the micro-reactor of FIG. 1a along line AA'.

The two layers 102 and 104 are bonded together, and at the first channel the first and the second layer are separated by a first distance 130. Similarly at the second channel the first and the second layer are separated by a second distance 132, which preferably equals the first distance. At the gap a third distance separates the first and the second layer, the third distance being smaller than the first and second distance.

As can be seen from these figures in a preferred embodiment the gap can be described by three dimensions along mutually perpendicular directions: the third distance or height along line DD', a length forming the distance between the first and the second channel along line AA' and a width perpendicular to the both DD' and AA'. However, other forms including irregular gaps can be used as well.

The first layer, for example a glass plate, shows the window 120 through which for example an optical microscope can observe/inspect particles and/or cells. Further a second area 122 can be used to observe the particles and/or cell with less detail, or with another method of observation.

A fluid containing the particles and/or cells to be inspected is fed to the inlet 112 and bled from outlet 114, so that a continuous stream of the fluid flows through the first channel. With observation means, for example a fluorescent microscope observing observation area 122, a decision is made whether a particle or cell of interest passes. If this is the case, and compensating for the time delay as a result of the distance between the window 120 and the observation area 122, the particle or cell can be sucked into the gap by applying a slight overpressure to the first channel or a slight under pressure to the second channel, or a combination thereof. The latter may be advisable to minimize changes of the gap height due to the pressure change.

It is noted that window 120 may give a view to a small part of the gap, or may comprise the whole or almost the whole gap.

It is also noted that transport of particles and/or cells may take place from the first to the second channel, but also in the other direction by applying a fluid with the cells and/or particles to the second channel.

It is further noted that at the window and (if implemented) at the observation area one layer, for example the first layer, must be transparent to the method of observation, but that the other layer may be covered with a reflective layer.

It is mentioned that, although in this embodiment a dynamic gradient (a pressure difference) is applied as a result of an observation at the observation area, the micro-reactor can also be used with a static gradient over the gap.

It is also mentioned that the gradient may be a pressure gradient, but also a chemical or biochemical additive to one of the two fluids, an electrical gradient, etc. Especially the use of so-named attractor fluids, such as cytokines and more specifically chemokines, showed to be effective to lure cells to cross the gap.

It is noted that in this embodiment the layer of adhesive holding the first and the second layer together is assumed to have a negligible thickness. Adhesive thicknesses with non-negligible thickness may be used, and applied to all places with the exception of the gap. Especially when the adhesive comprises, for example, spacers in e.g. the form of small spheres, this result in a simple way to produce micro-reactors with a well controlled gap height.

It is noted that the channels 106 and 108 may or may not be covered with the adhesive.

The gap 113 is free from adhesive, and as a result, when bonding the first and the second layer together, the thickness of the gap equals the thickness of the adhesive layer, that is controlled by the spheres in the adhesive. As will be recognized by the skilled person, as an alternative the adhesive can be applied to the first layer, again keeping the gap free of adhesive, and again bonding them together.

It should be mentioned that preferably a glass should be used that does not show fluorescence (so-named auto-fluorescent glasses), as this would hinder or disable the fluorescence of labels or materials in the fluid.

A method of operating the micro-reactor of FIG. 1 is by applying a fluid to the first channel, and applying a fluid in the second channel. The fluid in the first channel has a flow, and is inspected, for example at observation area 122. The inspection may comprise fluorescent microscopy, optical microscopy, but also, for example, X-ray inspection or radiological inspection for, for example, radio-active markers and/or materials. On the basis of this inspection/observation a decision can be made whether or not an inspection of the particles or cells in the gap is warranted or not.

This method is particularly useful when, for example, cells or molecules (such as proteins) are labeled with for example fluorescent labels, and the presence (or colour) of such a label is used to make the decision.

As the flow rate is known, it is also known when the observed and selected particles or cells pass the gap. At that moment a dynamic gradient between the first and the second channel can be applied, such as a pressure difference by temporarily lowering of the pressure in the second channel. As a result the selected particles or cells are sucked in the gap. In the gap the particles and/or cells can be observed with an optical microscope, a fluorescent microscope, a confocal microscope, or such like. Due to the small height of the gap the depth of focus of the microscope can be chosen to coincide with the gap height, and thus all particles/cells will be in focus. As an alternative, due to the small height, no particles will be stacked upon each other and e.g. the contours of a particle can be determined without overlap by another particle.

Another method of using the micro-reactor occurs when a static gradient is applied over the gap. The gradient may, for example, be a gradient in the concentration of a chemical, a gradient in the concentration of a biological material, a gradient in pressure, a gradient in temperature, or a gradient in electrical potential. In this case no observation is used to select cells and/or particles.

This method is, for example, useful for coaxing cells to pass through the gap. This process is known to happen when cells in a first fluid detect a substance in a fluid in the second channel. It is noted that it is possible to have cells from one type travel from the first channel to the second channel, while simultaneously cells of another type travel from the second channel to the first channel.

It is also noted that both the micro-reactor itself and the methods work equally well when the fluid enters via an outlet and leaves via an inlet: inlet and outlet are completely exchangeable.

FIG. 2a schematically shows a micro-reactor suited for STEM.

The micro-reactor shown in FIG. 2a can be thought to be derived from the micro-reactor shown in FIG. 1a. The first layer shows a recess 200 at the side that is not facing the second layer at the position of the window. As a result the first layer is, at the position coinciding with the window, sufficiently thin for a beam of e.g. electrons as used in a STEM to penetrate through the first layer. Electrons impinging on any material in the gap generate secondary radiation, such as back-scattered electrons, X-rays, or fluorescent light, to be detected outside the micro-reactor.

It is noted that, due to the short travel distance of electrons in solid matter, the thickness of the first layer and, especially when using a liquid, the height of the gap must be kept rather small. As an example: the typical penetration range of 300 keV electrons is 5 µm in water.

In principle also SEM can be used, but in that case the penetration range, using an electron beam with an energy of e.g. 30 keV, is typically limited to 500 nm.

It is noted that gaps with a larger third distance (a larger height) may be used, but that particles and structures further removed from the window will be invisible.

FIG. 2b schematically shows a cross-section of the micro-reactor shown in FIG. 2a along line AA'. As can be seen the thickness of the first layer is locally reduced to form a window with as little window material as possible.

FIG. 3 schematically shows a cross-section of a micro-reactor suited for TEM.

This micro-reactor can be thought to be derived from the micro-reactor shown in FIG. 2, more specifically FIG. 2b. Here also the second layer has a recess 300 opposite to the first recess a recess, the two recesses thus sandwiching the gap. As a result now also electrons travelling through the first recess, the fluid and the second recess can be detected. These transmitted electrons carry information in, for example, scattering angle and energy loss.

It is noted that the measurement or observation of a property, performed before the particles and or cells are brought into the gap, may be done with one technique, for example using optical microscopy or radiology, and the inspection in the gap with another technique, such as electron microscopy or X-ray inspection.

In a further method the cells or particles are immobilized in the gap, for example by freezing the fluid in which they are immersed. This can be done by, for example, immersing the micro-reactor in fluid ethane, or by spraying fluid ethane on the recess. The freezing may comprise the whole volume of the gap, or it may only comprise the entrance and/or outlet of the gap, leaving the cells and/or particles in a liquid. This may be important to avoid damage due to the freezing of the liquid.

In another method according to the invention the cells and/or particles are manoeuvred into the gap, then immobilized, e.g. by freezing of the fluid in which they are immersed, after which the micro-reactor is split in such a way that one of the layers is removed from the gap. This frees the particles or cells for inspection with techniques where the first layer hinders further inspection, such as SEM or FIB inspection. It also makes the cells and/or particles accessible for excision, so that a sample can be taken out of the material, and for example be inspected in a TEM, or, for example, a gas chromatograph. Many of such inspection methods are known to the skilled person.

We claim as follows:

1. A micro-reactor for observing particles or parts thereof in a fluid, while the micro-reactor is in a predetermined orientation, the micro-reactor comprising:
   a first and second layer, the first and second layers being horizontal in the predetermined orientation, the first layer having at least a first window that is transparent to visible light
   a first channel formed between the first and second layers for containing the fluid, the first channel having an inlet and an outlet both opening to an exterior of the microreactor, at the first channel the first and second layers being separated by a first distance,
   a second channel at least partially adjacent to the first channel, the second channel having an inlet and an outlet both opening to the exterior of the microreactor, the first and second layers at the second channel being separated by a second distance, the inlet of the second channel being distinct from the inlet and the outlet of the first channel, a gap directly connecting the first channel and the second channel along the adjacent portion, the gap formed within a channel wall common to the first and second channels, at the gap the first layer having a second window transparent to x-rays or charged particles, at the second window, the first and second layers being separated by a third distance smaller than the first distance and smaller than the second distance, and the third distance being equal to or smaller than 5 µm.

2. The micro-reactor of claim 1, wherein the second window is transparent to electrons.

3. The micro-reactor according to claim 1 in which at least a part of the micro-reactor is formed from glass.

4. The micro-reactor according to claim 1 in which the third distance is less than 300 nm.

5. The micro-reactor according to claim 1 in which the micro-reactor is constructed such that one of the first and second layers is removable from the gap.

6. A method of observing particles or parts thereof in a fluid by a method of inspection that includes transmitting at the fluid at least one of a group consisting essentially of x-rays and charged particles, and further comprising:

providing a micro-reactor including:

a first channel formed between first and second layers, and containing the fluid, the first channel having an inlet and an outlet both opening to an exterior of the micro-reactor, at the first channel the first and second layers being separated by a first distance, the first layer having at least a first window that is transparent to visible light, the first and second layers further being horizontal in the predetermined orientation, a second channel adjacent to the first channel along at least an adjacent portion, the second channel having an inlet and an outlet both opening to the exterior of the micro-reactor, the first and second layers at the second channel being separated by a second distance, the inlet of the second channel being distinct from the inlet and the outlet of the first channel, a gap directly connecting the first channel and the second channel along the adjacent portion, at the gap the first layer having a second window transparent to x-rays or charged particles, at the second window the first and second layers being separated by a third distance smaller than the first distance and smaller than the second distance, and the third distance being equal to or smaller than 5 µm;

optically viewing the liquid through the first window and finding an item warranting inspecting by the method of inspection;

moving the item of interest to the second window and inspecting the item of interest using the method of inspection.

7. The method of claim 6 wherein the item of interest is moved to the second window by fluid pressure.

8. The method of claim 6 wherein the item of interest is moved to the second window by creation of a chemical gradient.

9. The method of claim 6 in which the item of interest is immobilized in the gap.

10. The method of claim 6 in which the item of interest is in a solution and the item of interest is immobilized by freezing or polymerizing the solution.

11. The method of claim 10 in which the solution comprises water.

12. The method of claim 9 in which, after immobilizing the item of interest, the micro-reactor is split in such a way that one of the layers is removed from the gap, and the particles and/or the cells in the gap are inspected afterwards.

13. The method of claim 12 in which the method further comprises excising a part of the frozen or polymerized fluid in the gap, the excised part to be machined and/or inspected in an inspection tool.

14. The micro-reactor of claim 1, in which the gap is formed with a channel wall common to the first and second channels, the wall formed in the second layer between the first and second channels, with the gap bounded (in the predetermined orientation) at its bottom by the top of the wall and at its top by the second window, the wall positioned between the first and second channels at the adjacent portion.

15. The micro-reactor of claim 14 in which the wall is thinner than the first and second channels are wide, in the predetermined orientation.

16. The micro reactor of claim 1, in which the gap is formed with a channel wall common to the first and second channels, the wall formed in the second layer and positioned between the first and second channels at the adjacent portion, the wall having sloped sides and a flat top portion, the flat top portioned positioned under the second window in the predetermined orientation.

17. The micro-reactor of claim 16, in which the wall further includes a recess in the interior of the wall opening to the bottom of the second layer in the predetermined orientation.

18. The micro-reactor of claim 17, further comprising a transmission electron microscope directed at the second window and at the recess.

19. The micro-reactor of claim 1, in which the first and second channels are connected to each other only through the gap.

20. The micro-reactor of claim 1, further comprising an x-ray inspection device or charged particle inspection device directed at the second window.

21. The micro-reactor of claim 20, in which the inspection device is an x-ray inspection device.

22. The micro-reactor of claim 20, in which the inspection device is a scanning electron microscope (SEM).

23. The micro-reactor of claim 20, further comprising an optical inspection device directed at the first window.

24. The micro-reactor of claim 1 in which the first channel extends along a first portion from the first channel's inlet to the gap, then along the entire gap, and then along a second portion to the first channel's outlet.

* * * * *